US009323895B2

(12) United States Patent
Balinski et al.

(10) Patent No.: US 9,323,895 B2
(45) Date of Patent: Apr. 26, 2016

(54) HEALTHCARE MANAGEMENT

(71) Applicant: International Business Machines Corporation, Armonk, NY (US)

(72) Inventors: Peter A. Balinski, Elmhurst, NY (US); John G. Musial, Newburgh, NY (US); Sandeep R. Patil, Pune (IN); Riyazahamad M. Shiraguppi, Pune (IN)

(73) Assignee: International Business Machines Corporation, Armonk, NY (US)

( * ) Notice: Subject to any disclaimer, the term of this patent is extended or adjusted under 35 U.S.C. 154(b) by 256 days.

(21) Appl. No.: 13/906,563

(22) Filed: May 31, 2013

(65) Prior Publication Data

US 2014/0358568 A1      Dec. 4, 2014

(51) Int. Cl.
*G06Q 50/22* (2012.01)
*G06F 19/00* (2011.01)

(52) U.S. Cl.
CPC .......... *G06F 19/3406* (2013.01); *G06F 19/327* (2013.01)

(58) Field of Classification Search
CPC .......................................... G06Q 50/22–50/24
USPC ......................................................... 705/2–3
See application file for complete search history.

(56) References Cited

U.S. PATENT DOCUMENTS

| | | | |
|---|---|---|---|
| 6,236,317 B1 | 5/2001 | Cohen et al. | |
| 7,015,816 B2 * | 3/2006 | Wildman | G06F 19/3418 340/539.1 |
| 7,893,842 B2 | 2/2011 | Deutsch | |
| 8,046,172 B2 | 10/2011 | Kreiswirth et al. | |
| 8,128,608 B2 | 3/2012 | Thevenin | |
| 2006/0132316 A1* | 6/2006 | Wildman | G06F 19/3418 340/573.1 |
| 2007/0273499 A1 | 11/2007 | Chlubek et al. | |
| 2008/0209665 A1 | 9/2008 | Mangiardi | |
| 2008/0216879 A1 | 9/2008 | Johnson | |
| 2009/0151103 A1 | 6/2009 | Gallu | |
| 2009/0276239 A1 | 11/2009 | Swart et al. | |
| 2010/0088107 A1 | 4/2010 | Ur et al. | |
| 2011/0163870 A1 | 7/2011 | Snodgrass | |
| 2011/0191124 A1 | 8/2011 | Sung et al. | |
| 2011/0316695 A1* | 12/2011 | Li | G01S 5/02 340/539.13 |
| 2012/0116803 A1* | 5/2012 | Reid | A61L 2/28 705/2 |

(Continued)

OTHER PUBLICATIONS

Al Ameen et al., "Social Issues in Wireless Sensor Networks with Healthcare Perspective" The International Arab Journal of Information Technology, vol. 8, No. 1, Jan. 2011, pp. 52-58 [online], [retrieved on Jan. 3, 2012]. Retrieved from the Internet <URL: http://www.ccis2k.org/iajit/PDF/vol. 8,No. 1/10.pdf>.

(Continued)

*Primary Examiner* — Michael Tomaszewski
(74) *Attorney, Agent, or Firm* — James H. Mayfield; Jason H. Sosa

(57) ABSTRACT

A computer system obtains data from at least one sensor monitoring for health risk conditions, wherein a list of health risk conditions are pre-defined and stored in a server. The computer system determines that a health risk condition exists within an area based on the obtained data. The computer system determines a sanitization procedure for the health risk condition. The computer system initiates sanitization operations for the area according to the determined sanitization procedure.

11 Claims, 5 Drawing Sheets

(56) References Cited

U.S. PATENT DOCUMENTS

2012/0136221 A1 5/2012 Killen et al.
2012/0179479 A1* 7/2012 Waterson .............. G06Q 50/22
                                                    705/2

OTHER PUBLICATIONS

Dembry et al., "Strategies for Infection Control in Hospitals to Prevent the Spread of Infectious Diseases" Infection Control and Prevention, Touch Briefings 2008, European Infectious Disease, pp. 122-124 [online], [retrieved on Jan. 4, 2012]. Retrieved from the Internet <URL: http://www.touchbriefings.com/pdf/3187/viera.pdf>.

Leema et al., "Applying RFID Technology to construct an Elegant Hospital Environment" IJCSI International Journal of Computer Science Issues, vol. 8, Issue 3, No. 1, May 2011, pp. 444-448, www.IJCSI.org [online], [retrieved on Apr. 3, 2013]. Retrieved from the Internet <URL: http://www.ijcsi.org/papers/IJCSI-8-3-1-444-448.pdf>.

Ng et al., "Patient Tracking in Emergency Department Using RFID" Project No. RAP 4927, Submitted to the Faculty of the Worcester Polytechnic Institute, pp. 1-94 [online], [retrieved on Jan. 4, 2012]. Retrieved from the Internet <URL: http://m.wpi.edu/Pubs/E-project/Available/E-project-092106-125706/unrestricted/06A013I.pdf>.

* cited by examiner

| FUNCTIONAL AREA | DIVISION | RISK CATEGORY | ACCESS TIMES | CLEANING HOURS | CLEANING SERVICE TIMES |
|---|---|---|---|---|---|
| REF: WARD NAME | SURGICAL | VERY HIGH | 24/7 | | MONDAY TO SUNDAY |
| CLEANING FREQUENCY SCHEDULE | | | | | |
| CLEANING FREQUENCY/SCHEDLUE | FREQUENCY OF SERVICE | ELEMENTS | | | |
| MAIN WARD/ SIDE ROOMS | 1 x DAILY | DAMP CLEAN ALL SURFACES, EMPTY BINS, VACUUM FLOOR AND DAMP MOP FLOOR, CLEAN BED FRAMES WEEKLY. | | | |
| MAIN WARD/ SIDE ROOMS | 2 x DAILY | FULL CLEAN SINKS, EMPTY BINS. | | | |
| TREATMENT ROOMS UTILITIES | 1 x DAILY | DAMP CLEAN ALL SURFACES, EMPTY BINS, DUST CONTROL AND DAMP MOP FLOOR. | | | |
| BATHROOMS/ SHOWER ROOMS | 2 x DAILY | FULL CLEAN SINKS, TOILETS, URINALS, SPLASH BACKS, BINS, PARTITIONS, MIRRORS, DAMP MOP FLOOR. | | | |
| TOILETS | 3 x DAILY | FULL CLEAN SINKS, TOILETS, URINALS, SPLASH BACKS, BINS, PARTITIONS, MIRRORS, DAMP MOP FLOOR. | | | |
| GENERAL AREAS, CORRIDORS, CLEANERS CUPBOARDS | 1 x DAILY | DAMP CLEAN ALL SURFACES, EMPTY BINS, VACUUM FLOORS, DAMP MOP FLOOR. WIPE DOWN ALL CLEANING EQUIPMENT. | | | |
| WARD/KITCHEN | 1 x DAILY | FULL CLEAN SINKS, DAMP CLEAN ALL CUPBOARDS, CLEAN FRIDGE, EMPTY BINS, VACUUM FLOOR AND DAMP MOP FLOOR, DEFROST FRIDGE MONTHLY. | | | |
| OFFICES | 1 x WEEKLY | EMPTY BINS DAILY, DUST REMOVAL ALL SURFACES, CLEAN SINK, VACUUM CLEAN CARPET WEEKLY. | | | |
| DISPENSERS (HAND/GEL/PAPER) | 3 x DAILY | WIPE OVER OUTSIDE SURFACE, REPLENISH SOAP AND PAPER HAND TOWELS/TOILET TISSUE DISPENSERS, FULL CLEAN WEEKLY. | | | |
| SLUICE | 2 X DAILY | FULL CLEAN SINKS, TOILETS, SPLASH BACKS, BINS PARTITIONS, MIRRORS, DAMP MOP FLOOR. | | | |

TABLE 1 - A TYPICAL CLEANING SCHEDULE

FIG. 2

HEALTHCARE MANAGEMENT

BACKGROUND

The present invention relates to healthcare, and more specifically, to safer healthcare management, such as sanitization management of different facilities.

In general, very little information may be known or available concerning the health of an individual entering a location that is accessible to the public. For example, in a hospital environment, an individual may exhibit or develop symptoms that cause him to visit the hospital, though neither the individual nor hospital staff may be aware of the underlying conditions responsible for the symptoms. In another example, an individual may enter a restaurant with certain symptoms and the underlying conditions responsible for the symptoms may be contagious. For conditions that are highly contagious, it can be critical for the health and safety of others in the vicinity to ascertain this information as quickly as possible and to take immediate action to prevent the spread of infection.

SUMMARY

According to embodiments of the present invention, a method, system, and computer program product for managing health risk conditions are disclosed. A system obtains data from at least one sensor monitoring for health risk conditions, wherein a list of health risk conditions are pre-defined and stored in a server. The system determines that a health risk condition exists within an area based on the obtained data. The system determines a sanitization procedure for the health risk condition. The system initiates sanitization operations for the area according to the determined sanitization procedure.

BRIEF DESCRIPTION OF THE DRAWINGS

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

FIG. 2 is a table depicting an illustrative schedule;

DETAILED DESCRIPTION

According to exemplary embodiments, sanitization management is provided. A facility sanitization management provides the ability to dynamically track individuals with known or suspected conditions for the purpose of implementing timely clean-up processes for affected locations based on the nature of the conditions. The facility sanitization management directs clean-up processes to prevent the spread of infectious disease or other outbreak. The facility sanitization management monitors locations visited by individuals using a tracking mechanism and once a condition is determined, the facility sanitization management creates a clean-up job targeted for the specific locations. These and other features of the facility sanitization management will now be described.

Figure 1:
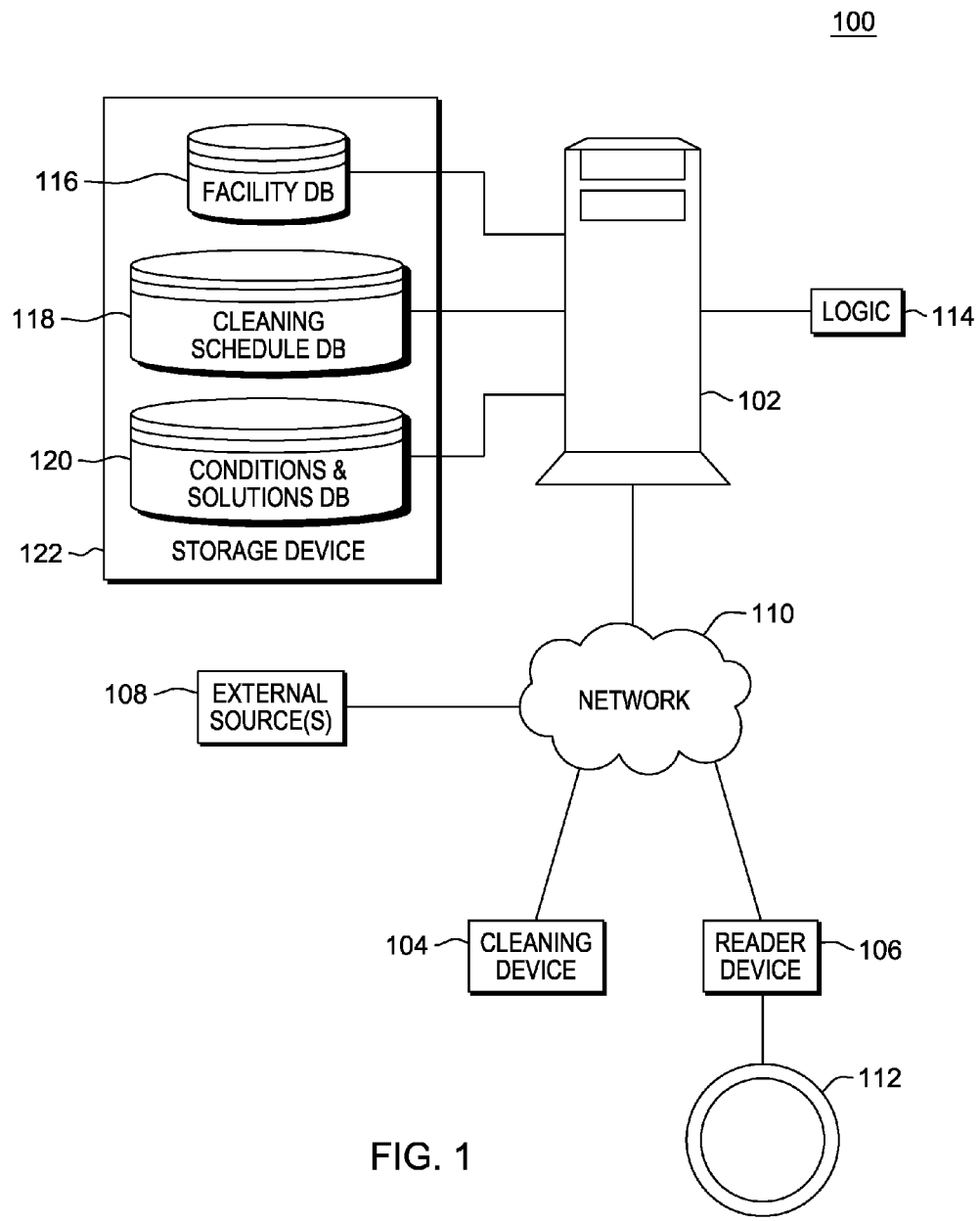
FIG. 1 depicts a block diagram of a system upon which sanitization management may be implemented according to an embodiment of the invention.

In reference to FIG. 1, an exemplary system 100, upon which the facility sanitization management may be implemented, is described according to an exemplary embodiment. A person skilled in the art will recognize that many variants of this system are possible and all such variations fall within the scope of this invention. System 100 of FIG. 1 includes a host system 102 in communication with a plurality of devices (e.g., cleaning device 104 and reader device 106) and one or more external sources, e.g., external source 108, over one or more networks 110. Reader device 106 may be a sensor, camera, mobile device, NFC device, or any other device capable of gathering information relative to its location.

The host system 102 may be implemented as a high-speed computer processing device (e.g., a mainframe computer) that is capable of handling a large volume of activities conducted by users of facility sanitization management. In another embodiment, host system 102 may be implemented as a system of computers and components that may collectively perform sanitization management processes. The host system 102 may be implemented, for example, by a medical facility (e.g., a hospital), or any establishment that renders services to individuals (e.g., a cruise ship company). It will be understood that the exemplary embodiments may be extended to offer healthcare management, hereinafter also referred to as sanitization management, to non-medical facilities, such as any establishment that comes in contact with the public (e.g., restaurants, manufacturing plants, etc.). Alternatively, the sanitization management may be administered by an application service provider (ASP) entity that provides the services to other establishments. In an exemplary embodiment, the host system 102 executes logic 114 for implementing the facility sanitization management described herein.

Cleaning device 104 in one embodiment may include an automated cleaning system. While only a single cleaning device 104 is shown in FIG. 1, it will be understood that any number of cleaning devices may be employed by the facility of the host system 102 in order to realize the advantages of the exemplary embodiments described herein. For example, if the establishment is a hospital, there may be one cleaning device 104 assigned to each room on a floor or each floor in the facility. In another example, if the establishment is a hotel, there may be one cleaning device 104 assigned to each floor or each wing in a floor. In one embodiment, multiple cleaning devices 104 performing differing functions may be employed. For example, one cleaning device 104 may be a dedicated, stationary device that is configured to perform a specific function (e.g., sterilization of equipment—medical equipment in a hospital or plates, spoons, etc., in a hotel), while another cleaning device 104 may include components configured to sanitize floors. Thus, the particular components of the cleaning device 104 may depend on its designated function(s). The cleaning device may include wheels for remote control of the movement of the cleaning device 104, wherein host system 102 may be configured to remotely operate cleaning device 104. Other components may include, in a non-exhaustive list, one or more of a wireless antenna, a control unit, motor, spray nozzle, cleaning fluid reservoir, laser unit, vacuum inlet, brushes, and sterile, disposable cartridges.

The reader device 106 may be any device capable of discerning conditions or attributes of its surrounding environment. For example, a device may have one or more sensors capable of receiving video and/or audio, detecting and measuring particulate in the air, detecting heat (body temperature for example), detecting vibrations (pulse), etc. Reader device 106 may be a stationary device positioned at specific location and detecting environmental factors surrounding it. In another embodiment, reader device 106 may move, for example a robot following a fixed pattern; or reader device 106 may be physically attached to a patient.

Reader device 106 may also communicate with a wireless tracking system, such as a radio frequency identification (RFID) reader or a sensor capable of tracking. For example, in a hospital environment, an individual (e.g., a patient) is provided with a patient bracelet or medical card having an RFID tag or any other sensor device embedded thereon, which is able to track the patient. For illustrative purposes, FIG. 1 shows a patient bracelet 112 communicatively coupled to the reader device 106. While only a single reader device 106 is shown in FIG. 1, the embodiments herein are not so limited. For example, there may be many reader devices 106 disposed in locations throughout the facility. In another embodiment, reader device 106 may include the wireless tracking system. For example, a medical bracelet capable of tracking a patient may also be able to take the patient's temperature and/or pulse.

If the tracking system employs RFID technology, the patient bracelet 112 or other device (e.g., a medical card) may include a control module and an antenna to communicate with reader device 106 and/or host system 102. The control module, in turn, may include a processor or logic controller, a modulator, a demodulator, a receiver, a transmitter, and a ground unit. The antenna may be a ferrite core antenna or any suitable antenna used in radio frequency transmissions. One skilled in the art will recognize that various other sensor devices using wireless technology to communicate may be implemented in place of an RFID device.

In an alternative embodiment, the tracking system may be implemented using a wireless, global positioning system-enabled communications device, such as a smart phone. In this embodiment, the individual may be tracked using signals received from the communications device indicative of coordinates for the location in which the individual is situated using, e.g., cellular, WiFi, Bluetooth® and/or other wireless communication protocols.

In an embodiment, the external sources 108 may be information sources that provide up-to-date data on infectious diseases or other risks that can be caused by unhygienic conditions or any contagious conditions. For example, the external sources 108 may include searchable databases implemented by the World Health Organization (WHO), Centers for Disease Control (CDC), and Occupational Safety and Health Administration (OSHA), or may be a news feed that provides current information on a discovered health risk. The host system 102 may communicate with these external sources 108 over one or more networks 110.

In an exemplary embodiment, the host system is communicatively coupled to a storage device 122 that houses various databases used in implementing sanitization management. The databases include a facility database 116, a cleaning schedule database 118, and a conditions database 120. An exemplary illustration of a cleaning schedule for a hospital environment may be as presented in Table 1—depicted in FIG. 2. One skilled in the art will recognize that various other formats of a cleaning schedule may be provided depending on the place where sanitization management is being undertaken. For example, in a hotel environment, the schedule would be completely different from that presented in Table 1 for a hospital environment. It should also be noted that the parameters indicated are exemplary in nature and depending on the place/area, the parameters used for defining the schedule can vary in nature.

The facility database 116 stores particular information relating to the facility subject to the sanitization management. In an exemplary embodiment, users of the host system 102 using, e.g., a user interface provided by logic 114, may create facility database 116. In one embodiment, based on historical data maintained, the host system may automatically create facility database 116 and provide to the user for approval. For example, facility database 116 may store user-defined identifiers for areas, structures within the areas, and materials associated with the structures, which may be in the form of structured or unstructured data. In addition, facility database 116 may be configured by a user to store identifiers of one or more cleaning devices 104 and one or more reader devices 106 that are assigned by the user to areas of the facility.

For example, a sample data structure used in implementing the facility database is shown as follows:

Area_ID
Structure_ID
Material_ID
Clean_Device_ID
Reader_ID

The area may be defined as a floor, a room, a portion of a room, or a combination thereof. For example, one area identifier may be assigned to a patient waiting room. It will be understood that multiple reader devices 106 and/or multiple cleaning devices 104 may be assigned to a single area depending on the needs of the facility.

Cleaning schedule database 118 stores a listing of routine cleaning services that may be performed for the facility broken down by area. The listing of cleaning services may also include a frequency of cleaning (e.g., once per week, daily, etc.), as illustrated in Table 1. There may be multiple procedures scheduled for each area where each procedure represents a particular task (e.g., damp mop floor, dust surfaces, empty bins, etc.). In one embodiment, the cleaning services may also include one or more types of solutions (cleaning agents) to be used in each procedure based on the function associated with the area. For example, in a room where samples of patient's blood are taken, the solutions may require a fluid that includes a percentage of spirit or bleach sufficient to eliminate any potential organisms that may be found in blood residue that is inadvertently left on any structure within the area. Thus, if an area is associated with a function that may result in contamination of the area, the cleaning services may specify particular tasks or procedures. One of ordinary skill in the art will recognize that any cleaning agents effective against a detected condition may be used.

In an exemplary embodiment, logic 114 is configured to enable access of the cleaning schedule database 118 when creating a job to identify routine cleaning procedures and associated solutions. Logic 114 may select from these solutions based on a given condition identified for a location in the facility, as will be described further herein.

The conditions and solutions database 120 stores conditions indicative of various risks, for example health risks, along with associated solutions designed to eliminate elements of the condition within a contaminated area. For example, conditions and solutions database 120 may store a listing of infectious diseases or unhygienic conditions and any substances or techniques known for treating contaminated areas. Examples of substances may include ultraviolet rays, phenol, chemical wash, and anti-bacterial sanitizer, to name a few. The form of application of such substances may also be configured via logic 114. For example, the form of application may include spray, scrub, soak, etc.

Network 110 may include any type of network, such as a local area network, wide area network, virtual private network, and the Internet. In addition, network 110 may be configured to support wireless communications, e.g., via cellular networks, satellite networks, global positioning systems, and short-range wireless communications, such as WiFi and Bluetooth.

Host system 102 is communicatively coupled to storage device 122 storing various data used in implementing the management services. For example, storage device 122 may store management models, performance histories, and other desired information that can be used at a future point in time or as a reference at any given point in time, when sanitization management conditions occur. Storage device 122 may be directly in communication with the host system 102 (e.g., via cabling) or may be logically addressable by host system 102, e.g., as a consolidated data source over network 110.

Figure 3:
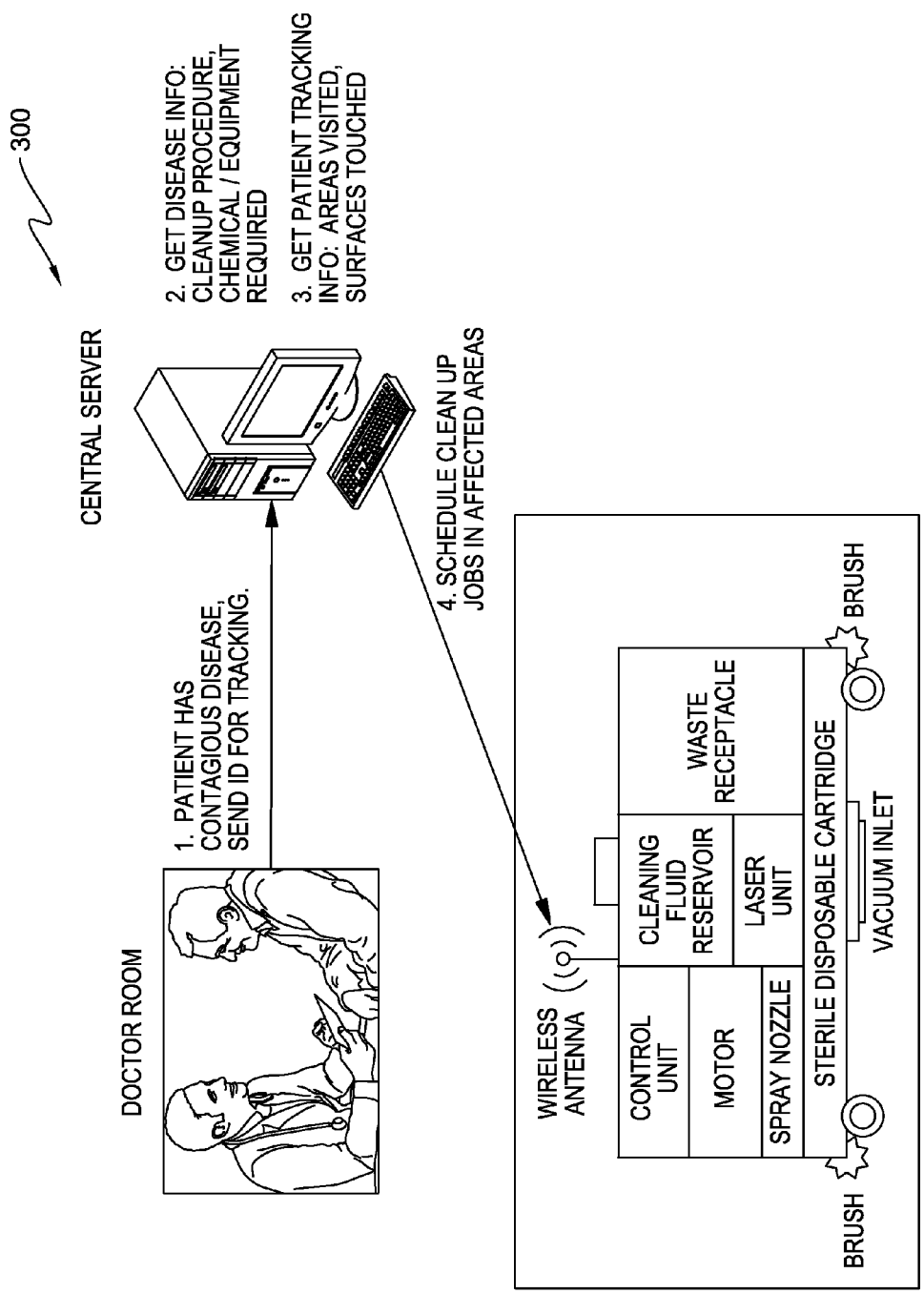
FIG. 3 depicts an exemplary embodiment describing a process for implementing hospital sanitization management.

Turning now to FIG. 3, an exemplary embodiment is depicted and describes process 300 for implementing facility sanitization management. FIG. 3 shows a typical flow of operation in the proposed system 100 where, for example, a patient, visiting a hospital or a clinic, is tracked. For example, the visiting patient may be given a tracking device such as an RFID tag, as illustrated in FIG. 1. The patient can now be tracked over the area of the hospital that the patient is visiting by monitoring the movements of the patient in the premise and transmitting such movements to a central server.

The central server is configured to receive the conditions of the patient (e.g., a doctor may enter a diagnosis for the patient. The tracking device may be coupled to one or more sensors that relay information to the central server or, as the patient traverses the hospital, one or more sensors may identify the patient via the tracking device and determine one or more conditions and send the conditions to the central server). The central server suggests a specific clean up procedure, a chemical required in the clean up process, and specific equipment required for the clean up process. The central server is configured to prepare cleanup jobs, and in one embodiment, the central server schedules the cleanup jobs for the affected areas. In one embodiment, the server can track where such equipment is located and request equipment from the closest location to reach the place that requires sanitization. The server identifies the required sanitization associated with the unhygienic conditions and notifies the automatic cleaning device. The automatic cleaning device may have several components, such as a wireless transmitter, to communicate with the server, for example, to receive a schedule at the automatic cleaning device, or other instructions. The automatic cleaning device may then perform the sanitization management as per the schedule. A motor drives the cleaning device and can be tracked using the wireless transmitter on the automatic cleaning device. The automatic cleaning device may include other units used for sanitization management such as a laser unit, spray, waste replacement, etc. One skilled in the art will recognize that the automatic cleaning device is only exemplary in nature and various other modifications may be made to such a device to efficiently perform the task of sanitization management.

Figure 4:
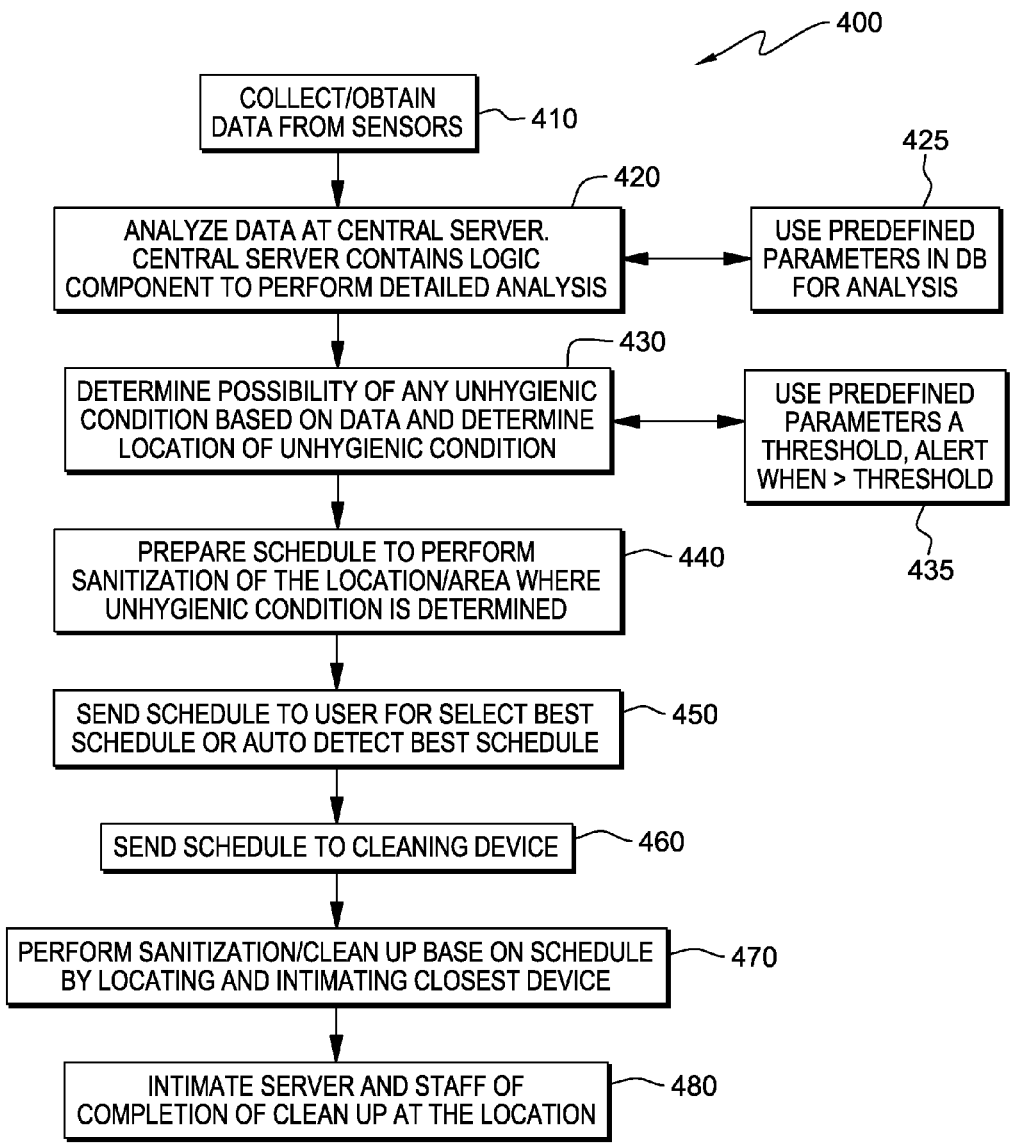
FIG. 4 depicts a general flow diagram describing a process for implementing facility sanitization according to another embodiment of the present invention.

FIG. 4 illustrates an exemplary flow diagram 400 describing a process for sanitization management.

At step 410, data is obtained from sensors placed in a given area, wherein the sensors gather data and transmit the data to a central server. For example, consider a hospital environment, where a patient enters the hospital. The patient is first tagged with a tracking device, such as bracelet 112. The tracking device may be programmed to store a patient identifier that is mapped to a back-end patient database (not shown) of host system 102. In another embodiment, consider a public place such as a restaurant, wherein people are entering and leaving. Sensors can be placed at various locations to monitor the hygiene of a given area periodically. Collected data may be transmitted to a central server. In such a case, specific areas may be targeted instead of the patient. In various embodiments, sensors can detect paleness, jaundice, excessive sweating, temperature, heart rate, sneezing, coughing, weakness of breath, wheezing, and, in some cases, can even identify and measure particulate in the air.

At step 420, data collected from the sensors are analyzed at the server. In step 430, the server categorizes the data to determine any unhygienic conditions or high levels of contamination that are beyond a pre-defined threshold, and marks the specific location where such a condition prevails. The original analysis can be performed based on predefined parameters, for example, conditions characterized in conditions and solutions database 120 of FIG. 1. The sanitization process may monitor potential symptoms of a person within an area or conditions within an area (e.g., via reader device 106) and compare the symptoms and/or conditions to known conditions. Based on the condition determined, the server is configured to mine for historical data, check for solutions, and prepare a schedule to sanitize the area (step 440). If the situation is an unrecognized condition, but recognized as a potential threat, the process may search external sources 108 for solutions, or may choose an aggressive course of action in an effort to maintain healthy conditions within the area.

In step 450, the prepared schedule is sent to a user to be approved or the best solution may be chosen by the server based on heuristics or intelligence programmed for the server to select the best possible schedule for sanitizing the facility. In step 460, the schedule is transmitted to the cleaning device, such as an automated cleaning device shown in FIG. 2. Based on the schedule and the location, the cleaning device performs the required sanitization (step 470) at the facility determined or the area where the unhygienic conditions are determined. In step 480, the responsible staff of the facility is notified that the sanitization process is complete.

For example, consider that a patient enters a hospital. Once the patient has entered, the patient is tagged, e.g., with a tracking device, such that the patient can be tracked/monitored within the hospital premise. The patient is diagnosed with a form of contagious ailment, or preliminarily diagnosed (e.g., based on symptoms presented), with a contagious ailment (also referred to herein as a condition). The diagnosis may be stored in a patient record with the patient identifier in the patient database or may be stored in a portable electronic device with the patient. When the patient enters the hospital with such a device, data can be collected by sensors using NFC (Near Field Communication) or other wireless means. The logic in the server determines whether the ailment is on the list stored in the conditions database. The list of ailments may include symptoms that are considered a potential risk for spread of infection.

If the ailment is not on the list, this means it is not considered a risk to other individuals in the facility, and the process ends. Otherwise, if the ailment is on the list the logic tracks movement of the patient within the facility. As indicated above, this tracking may, in one embodiment, be implemented using RFID technologies in which the reader device(s) communicating with the tracking device (e.g., bracelet), and sends this information (e.g., reader identifier(s) and patient identifier) to the host system or central server. The logic accesses the facility database and determines the location(s) visited using this information from the reader device(s).

The logic on the central server uses the condition, or information to search the conditions database for a solution configured to decontaminate the locations, and identifies structures and materials associated with the locations visited by the patient. Identification is performed by searching the facility database using identifiers of the areas and/or reader devices and retrieving the associated structure and material information. The structures and materials associated with the locations may impact how the areas are treated. For example, tile flooring may be scrubbed using a fluid solution, while a fabric covered patient chair may be sprayed using a different solution, as illustrated in the automatic cleaning device shown in FIG. 2.

The logic creates one or more clean-up jobs (schedules) for the identified locations based on the selected solutions and structures/materials. In one embodiment, the logic may be configured to prioritize procedures for a clean-up job as well as the clean-up jobs themselves. In some situations, it may be necessary to create multiple clean-up jobs based on the severity of the contamination and/or the severity of the condition. The logic may be configured to prioritize clean-up jobs based on a priority value assigned to a condition or location of the contamination. The priority value may indicate that a clean-up must be performed immediately. Other priority values may provide an ordering of the clean-up jobs based on the severity of the condition or the severity of the spread of the condition.

For example, suppose that a patient with a highly infectious condition enters a patient waiting room and then subsequently enters an area in which immune-deficient patients (e.g., infants or elderly) are located. The logic may be configured to assign a highest priority to the area in which the immune-deficient patients are located; thus, the priority is assigned based on a perceived health threat to a population of patients. Alternatively, or in conjunction therewith, the priority may be assigned based on the average volume of patients that visit a particular area each day, whereby areas known to have higher traffic than other areas may be given higher priority to a clean-up schedule than low traffic areas.

The logic identifies the cleaning device(s) assigned to the affected locations (e.g., via the facility database and area identifiers), and assigns priority values to each of the clean-up jobs. It then dispatches the cleaning device(s) for the clean-up job at the top of the priority list, and applies a clean-up procedure as indicated in the clean-up job (e.g., scrub floor, sanitize hospital instruments, etc.). It further determines if all procedures for the first clean-up job(s) have been completed (e.g., by a signal received from the cleaning device).

In addition to scheduling clean-up jobs, the logic may be configured to determine and implement a quarantine plan of action based on the nature of the condition. For example, information from the external sources (e.g., news feed) may provide information as to the location of a detected condition or outbreak. Another external source (e.g., WHO database) may indicate a safe distance from a location of the condition in which individuals must maintain in order to prevent infection. For example, suppose the distance is 10 meters, then the logic in the central server may alert patients, staff, or other individuals (e.g., through existing intercom systems) who are located inside of this distance to remain in their current location to prevent further outbreaks.

Technical effects of the invention provide the ability to dynamically track individuals with known or suspected conditions for the purpose of implementing timely clean-up processes for affected locations based on the nature of the conditions. Sanitization management directs a clean up process to prevent the spread of infectious or unhygienic conditions or other outbreak. The sanitization management method monitors locations visited by individuals using a tracking mechanism and once a condition is determined, the facility sanitization management creates a clean-up job targeted for the specific locations.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. A computer readable storage medium may be, for example, but not limited to, an electronic, magnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 5:
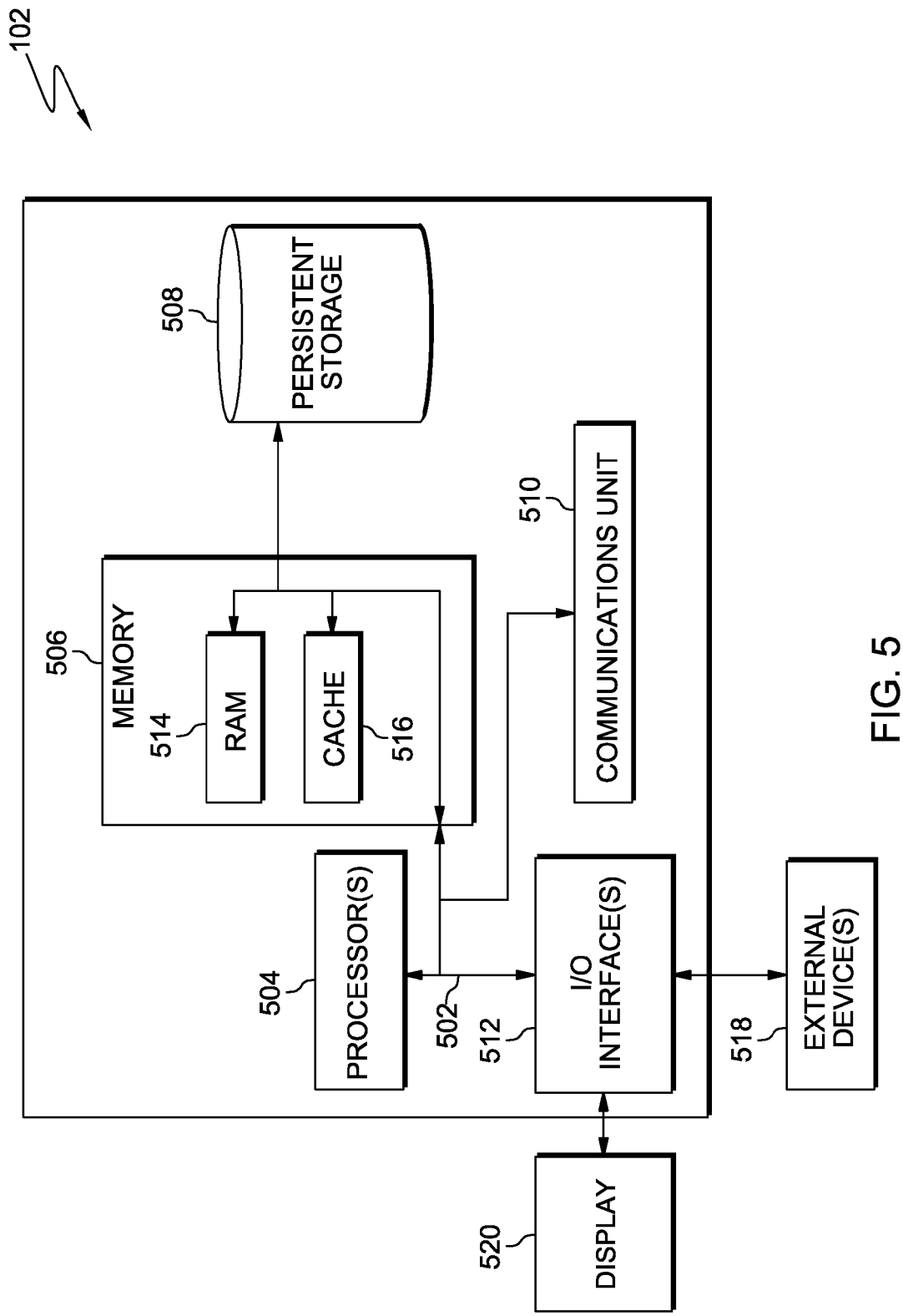
FIG. 5 depicts a block diagram of components of an exemplary computer system for implementing embodiments of the present invention.

FIG. 5 depicts a block diagram of components of host system 102, in accordance with an illustrative embodiment of the present invention. It should be appreciated that FIG. 5 provides only an illustration of one implementation and does not imply any limitations with regard to the environments in which different embodiments may be implemented. Many modifications to the depicted environment may be made. For example, host system 102 may comprise components spread through multiple systems and resources and may provide systems and resources beyond what is necessary to operate embodiments of the present invention.

Host system 102 includes communications fabric 502, which provides communications between computer processor(s) 504, memory 506, persistent storage 508, communications unit 510, and input/output (I/O) interface(s) 512. Communications fabric 502 can be implemented with any architecture designed for passing data and/or control information between processors (such as microprocessors, communications and network processors, etc.), system memory, peripheral devices, and any other hardware components within a system. For example, communications fabric 502 can be implemented with one or more buses.

Memory 506 and persistent storage 508 are computer-readable storage media. In this embodiment, memory 506 includes random access memory (RAM) 514 and cache memory 516. In general, memory 506 can include any suitable volatile or non-volatile computer-readable storage medium.

Logic 114 may be stored in persistent storage 508 for execution by one or more of computer processors 504 via one or more memories of memory 506. In this embodiment, persistent storage 508 includes a magnetic hard disk drive. Alternatively, or in addition to a magnetic hard disk drive, persistent storage 508 can include a solid state hard drive, a semiconductor storage device, read-only memory (ROM), erasable programmable read-only memory (EPROM), flash memory, or any other computer-readable storage medium that is capable of storing program instructions or digital information.

The media used by persistent storage 508 may also be removable. For example, a removable hard drive may be used for persistent storage 508. Other examples include optical and magnetic disks, thumb drives, and smart cards that are inserted into a drive for transfer onto another computer-readable storage medium that is also part of persistent storage 508.

Communications unit 510, in these examples, provides for communications with other data processing systems or devices, including systems and devices within or controlled by host system 102. In these examples, communications unit 510 includes one or more wireless network interface cards. Communications unit 510 may provide communications through the use of either or both physical and wireless communications links. Computer programs and processes, such as logic 114, may be downloaded to persistent storage 508 through communications unit 510.

I/O interface(s) 512 allows for input and output of data with other devices that may be connected to host system 102. For example, I/O interface 512 may provide a connection to external devices 518 such as a keyboard, keypad, a touch screen, and/or some other suitable input device. External devices 518 can also include portable computer-readable storage media such as, for example, thumb drives, portable optical or magnetic disks, and memory cards. Software and data used to practice embodiments of the present invention can be stored on such portable computer-readable storage media and can be loaded onto persistent storage 508 via I/O interface(s) 512. I/O interface(s) 512 may also connect to a display 520.

Display 520 provides a mechanism to display data to a user and may be, for example, a touch screen or a computer monitor.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow.

What is claimed is:

1. A system for managing health risk conditions, the system comprising:
   one or more computer processors;
   one or more sensors communicatively coupled to the one or more computer processors;
   one or more computer readable tangible storage media;
   one or more motor-driven, mobile automated cleaning devices communicatively coupled to the one or more computer processors;
   program instructions stored on the computer readable tangible storage media, which when executed by the one or more computer processors, perform the actions of:
   obtaining data from at least one sensor, of the one or more sensors, monitoring for health risk conditions, wherein a list of health risk conditions are pre-defined and stored on at least one of the one or more computer readable tangible storage media;
   obtaining patient history data from at least one sensor, of the one or more sensors, indicating a history of locations visited by a person;
   determining that a health risk condition exists within an area based on the obtained data, wherein the area is a location visited by the person;
   responsive to determining that the health risk condition exists, determining a sanitization procedure for the health risk condition;
   initiating sanitization operations for the area according to the determined sanitization procedure by using a motor-driven, mobile automated cleaning device of the one or more motor-driven, mobile automated cleaning devices; and
   cleaning the area using the motor-driven, mobile automated cleaning device, wherein the motor-driven, mobile automated cleaning device responds to the health risk condition according to the data from the at least one sensor of the one or more sensors.

2. The system as claimed in claim 1, wherein the at least one sensor monitors the area for health risk conditions based on perceived events occurring within the area.

3. The system as claimed in claim 1, wherein the at least one sensor monitors a person for health risk conditions based on one or more perceived actions of the person, body functions of the person, paleness, jaundice, excessive sweating, temperature, heart rate, sneezing, coughing, weakness of breath, wheezing, air particulates, and vital signs of the person.

4. The system as claimed in claim 1, wherein said determining the sanitization procedure for the health risk condition comprises:
   determining severity of the health risk condition;
   determining at least one cleaning agent effective against the health risk condition; and
   based on the severity of the health risk condition, scheduling a cleaning of the area with the at least one cleaning agent.

5. The system as claimed in claim 4, wherein said determining the sanitization procedure further comprises:
   determining at least one surface type of the area; wherein determining the at least one cleaning agent effective against the health risk condition is further based on the at least one surface type.

6. The system as claimed in claim 1,
   wherein said initiating sanitization operations for the area according to the determined sanitization procedure comprises:
   locating a motor-driven, mobile automated cleaning device, of the one or more motor-driven, mobile automated cleaning devices, proximate to the area and capable of performing the sanitization procedure; and
   electronically communicating to the motor-driven, mobile automated cleaning device to begin at a scheduled time.

7. The system as claimed in claim 1, wherein said initiating sanitization operations for the area according to the determined sanitization procedure comprises:
   notifying staff of the health risk condition and the determined sanitization operation.

8. A computer program product comprising:
   one or more computer readable tangible storage media; and
   program instructions stored on the one or more computer readable tangible non-transitory storage media, the program instructions comprising:
   program instructions to obtain data from at least one sensor monitoring for health risk conditions, wherein a list of health risk conditions are pre-defined;
   program instructions to obtain patient history data from at least one sensor, of the one or more sensors, indicating a history of locations visited by a person;
   program instructions to determine that a health risk condition exists within an area based on the obtained data, wherein the area is a location visited by the person;
   program instruction to determine a sanitization procedure for the health risk condition;
   program instructions to initiate sanitization operations for the area according to the determined sanitization procedure by using a motor-driven, mobile automated cleaning device of one or more motor-driven, mobile automated cleaning devices communicatively coupled to the one or more computer processors; and
   program instructions to clean the area using the motor-driven, mobile automated cleaning device, wherein the program instructions to clean the area comprise program instructions for the motor-driven, mobile automated cleaning device to respond to the health risk condition according to the data from the at least one sensor of the one or more sensors.

9. The computer program product as claimed in claim 8, wherein the at least one sensor monitors one or both of: the area for health risk conditions based on perceived events occurring within the area, and a person for health risk conditions based on one or more perceived actions of the person, body functions of the person, paleness, jaundice, excessive sweating, temperature, heart rate, sneezing, coughing, weakness of breath, wheezing, air particulates, and vital signs of the person.

10. The computer program product as claimed in claim 8, wherein the program instructions to determine the sanitization procedure for the health risk condition comprise instructions to:
  determine severity of the health risk condition;
  determine at least one cleaning agent effective against the health risk condition; and
  based on the severity of the health risk condition, schedule a cleaning of the area with the at least one cleaning agent.

11. The computer program product as claimed in claim 8, wherein the program instructions to initiate sanitization operations for the area according to the determined sanitization procedure comprise instructions to:
  locate a motor-driven, mobile automated cleaning device, of the one or more motor-driven, mobile automated cleaning devices, proximate to the area and capable of performing the sanitization procedure; and
  electronically communicate to the motor-driven, mobile automated cleaning device to begin at a scheduled time.

* * * * *